(12) United States Patent
Deal (10) Patent No.: US 7,682,401 B2
(45) Date of Patent: Mar. 23, 2010

(54) URETERAL STENT

(75) Inventor: Travis Deal, Freedom, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1381 days.

(21) Appl. No.: 11/102,644

(22) Filed: Apr. 11, 2005

(65) Prior Publication Data

US 2006/0229705 A1    Oct. 12, 2006

(51) Int. Cl.
*A61F 2/04* (2006.01)
*A61M 5/00* (2006.01)

(52) U.S. Cl. .................................. 623/23.66; 604/8
(58) Field of Classification Search ............ 604/8; 623/23.66
See application file for complete search history.

(56) References Cited

U.S. PATENT DOCUMENTS

| | | | |
|---|---|---|---|
| RE29,343 E | 8/1977 | Amplatz | |
| 4,568,338 A | 2/1986 | Todd | |
| 4,643,716 A | 2/1987 | Drach | |
| 4,738,667 A | 4/1988 | Galloway | |
| 4,790,810 A | 12/1988 | Pugh, Jr. | |
| 4,923,061 A | 5/1990 | Trombley, III | |
| 4,950,228 A | 8/1990 | Knapp, Jr. et al. | |
| 5,141,502 A | 8/1992 | Macaluso, Jr. et al. | |
| 5,647,843 A | 7/1997 | Mesrobian et al. | |
| 5,795,319 A | 8/1998 | Ali et al. | |
| 5,885,247 A | 3/1999 | Slagboom | |
| 2003/0195456 A1 | 10/2003 | Robertson | |
| 2004/0143209 A1 | 7/2004 | Liu et al. | |

OTHER PUBLICATIONS

International Search Report dated Aug. 10, 2006, for International Application No. PCT/US2006/006377, 4 pages.

*Primary Examiner*—Thomas J Sweet
(74) *Attorney, Agent, or Firm*—Cooley Godward Kronish LLP (57) ABSTRACT

A ureteral stent assembly includes an elongate member having a distal end portion for placement within a kidney of a patient and a proximal end portion for placement in at least one of a ureter of the patient and a bladder of the patient. The distal end portion has a retention portion configured to help retain at least a portion of the elongate member in the kidney of the patient. The elongate member is configured to be passed through the ureter of the patient from the kidney to the bladder to remove the elongate member from the patient. In one embodiment, the retention portion is configured such that a distal tip of the distal end portion of the ureteral stent is spaced from a sidewall of the ureter when the elongate member is passed through the ureter of the patient to remove the elongate member from the patient.

20 Claims, 10 Drawing Sheets

URETERAL STENT

BACKGROUND

The disclosed invention relates generally to a medical device assembly and more particularly to a ureteral stent.

Known ureteral stents are typically placed within a urinary tract of a patient such that one end portion of the ureteral stent is located in a kidney of the patient and another end portion of the ureteral stent is located in either a bladder or a ureter of the patient. Some known ureteral stents include retention members configured to help retain the ureteral stent in position within the patient. Known ureteral stents are typically positioned within the urinary tract of the patient by placing a guidewire within the patient, sliding the ureteral stent on the guidewire, and then forcing the ureteral stent along the guidewire into a desired position within the patient using a push rod. Such ureteral stents are often removed from the patient by pulling the ureteral stent from the urinary tract of the patient.

Known ureteral stents often cause discomfort to the patient once the ureteral stents are positioned within the body. Further discomfort can also result when the ureteral stent is being removed from a patient due to the configuration of the retention member. For example, in some known ureteral stents, the retention member has a coil shape that is intended to be unwound as the ureteral stent is being removed from the urinary tract of the patient. The retention members of some known ureteral stents, however, have the tendency to form a knot or a hook configuration during removal. Thus, the knot or the hook configuration drags along a sidewall of the ureter as the stent is being removed. In other situations, the end of the stent itself may drag along the sidewall of the ureter as the stent is being removed from the patient.

Thus, there is a need for a ureteral stent having a retention portion that is reconfigurable upon removal of the stent to help reduce pain and discomfort to the patient.

SUMMARY OF THE INVENTION

A ureteral stent assembly includes an elongate member having a distal end portion for placement within a kidney of a patient and a proximal end portion for placement in at least one of a ureter of the patient and a bladder of the patient. The distal end portion has a retention portion configured to help retain at least a portion of the elongate member in the kidney of the patient. The elongate member is configured to be passed through the ureter of the patient from the kidney to the bladder to remove the elongate member from the patient. In one embodiment, the retention portion is configured such that a distal tip of the distal end portion of the ureteral stent is spaced from a sidewall of the ureter when the elongate member is passed through the ureter of the patient to remove the elongate member from the patient.

BRIEF DESCRIPTION OF THE DRAWINGS

The present invention is described with reference to the accompanying drawings. In the drawings, like reference numbers indicate identical or functionally similar elements. For example item 100 is identical or functionally similar to item 100A.

DETAILED DESCRIPTION

Figure 1:
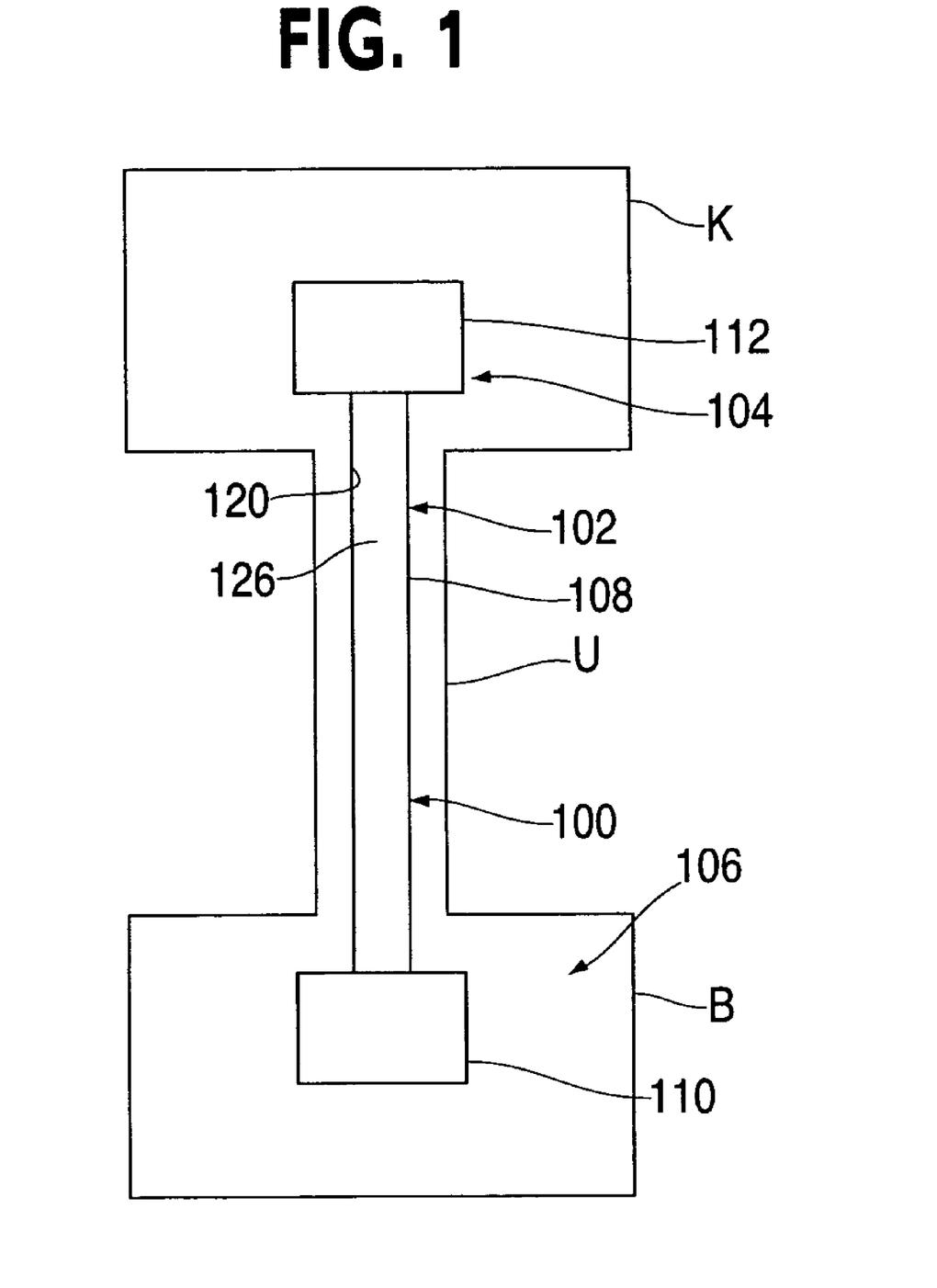
FIG. 1 is a schematic illustration of a ureteral stent according to an embodiment of the invention.

FIG. 1 is a schematic illustration of a ureteral stent 100 disposed within a urinary tract of a patient. Specifically, the ureteral stent 100 is placed or otherwise implanted into the urinary tract of a patient such that the ureteral stent 100 extends through the ureter U, from the kidney K of the patient to the bladder B of the patient. The ureteral stent 100 is configured to help facilitate the movement of fluid within a urinary tract of a patient.

The ureteral stent 100 includes an elongate member 102 having a distal end portion 104, a proximal end portion 106 and a medial portion 108 extending between the distal end portion 104 and the proximal end portion 106. The proximal end portion 106 includes a retention portion 110. Similarly, the distal end portion 104 includes a retention portion 112.

The retention portion 110 of the proximal end portion 106 of the ureteral stent 100 is configured to be placed within the bladder B of the patient and to help prevent migration of the ureteral stent 100 upwardly toward the kidney of the patient. Accordingly, the retention portion 110 is configured to help retain at least a portion of the ureteral stent 100 within the bladder B of the patient. Retention portion 110 may be configured in a variety of different shapes and sizes, but is generally sized such that it has a dimension sufficient to retain at least a portion of the elongate member 102 in the bladder of a patient. For example, the retention portion 110 of the proximal end portion 106 may include a loop portion, a "J" hook portion, a curled portion, a spiral portion, a pigtail portion, or any other structure that is configured to retain at least a portion of the ureteral stent 100 within the bladder B of the patient. Although the ureteral stent 100 is illustrated and described as including a retention portion 110, in other embodiments, proximal end portion 106 does not include a retention portion.

The retention portion 112 of the distal end portion 104 is configured such that it is reconfigurable between a retracted or unconstrained configuration when it is placed in the kidney K of the patient, and an extended or constrained configuration when it is being pulled or otherwise forced through the ureter U of the patient. When the retention portion 112 of the distal end portion 104 is in its retracted or unconstrained configuration, the retention portion 112 is configured to be placed within the kidney K of the patient and to help prevent migration of the ureteral stent 100 downwardly toward the bladder B. Accordingly, the retention portion 112 is configured to help retain at least a portion of the ureteral stent 100 within the kidney K of the patient when the retention portion 112 is in its retracted or unconstrained configuration. Retention portion 112 may be configured in a variety of different shapes and sizes, but is generally sized such that when the retention portion 112 is in its retracted or unconstrained configuration it has a dimension sufficient to retain at least a portion of the elongate member 102 in the kidney K of the patient.

When the retention portion 112 is in its extended or constrained configuration, the retention portion 112 is configured to assume a more linear or elongate, or less tortuous or arcuate, shape. The retention portion 112 is also configured such that when the ureteral stent 100 is removed from the patient by pulling or otherwise forcing the ureteral stent 100 through the urinary tract, the retention portion 112 is passed through the ureter U such that a distal end of the ureteral stent 100 is disposed away from the sidewall of the ureter U.

In the embodiment shown in FIG. 1, ureteral stent 100 includes a sidewall 120 that defines a lumen 126. The lumen 126 extends from the distal end portion 104 to the proximal end portion 106 of the ureteral stent 100. In other embodiments, the lumen does not extend from the distal end portion to the proximal end portion. Rather, the lumen only extends through a portion of the ureteral stent. In yet another embodiment, the ureteral stent does not include a sidewall that defines a lumen.

Although the ureteral stent 100 is illustrated and described as being configured to extend from the kidney K of the patient to the bladder B of the patient, it is not necessary that ureteral stent 100 be configured to extend from the kidney K to the bladder B. For example, in another embodiment, the ureteral stent is configured to extend from the kidney K of the patient to a location within the ureter U of the patient. In still another embodiment, the ureteral stent is configured to extend from the kidney K of the patient to a location outside of the body of the patient.

In one embodiment, ureteral stent 100 is implanted into the urinary tract of the patient by inserting the stent 100 into the patient transuretherally. For example, a guidewire may be placed within the urinary tract of the patient. Subsequently, the ureteral stent 100 may be placed on the guidewire and forced into a desired position within the urinary tract of the patient. In another embodiment, ureteral stent 100 is implanted into the urinary tract of the patient by inserting the stent 100 into the patient transdermally or percutaneously.

Figure 2A:
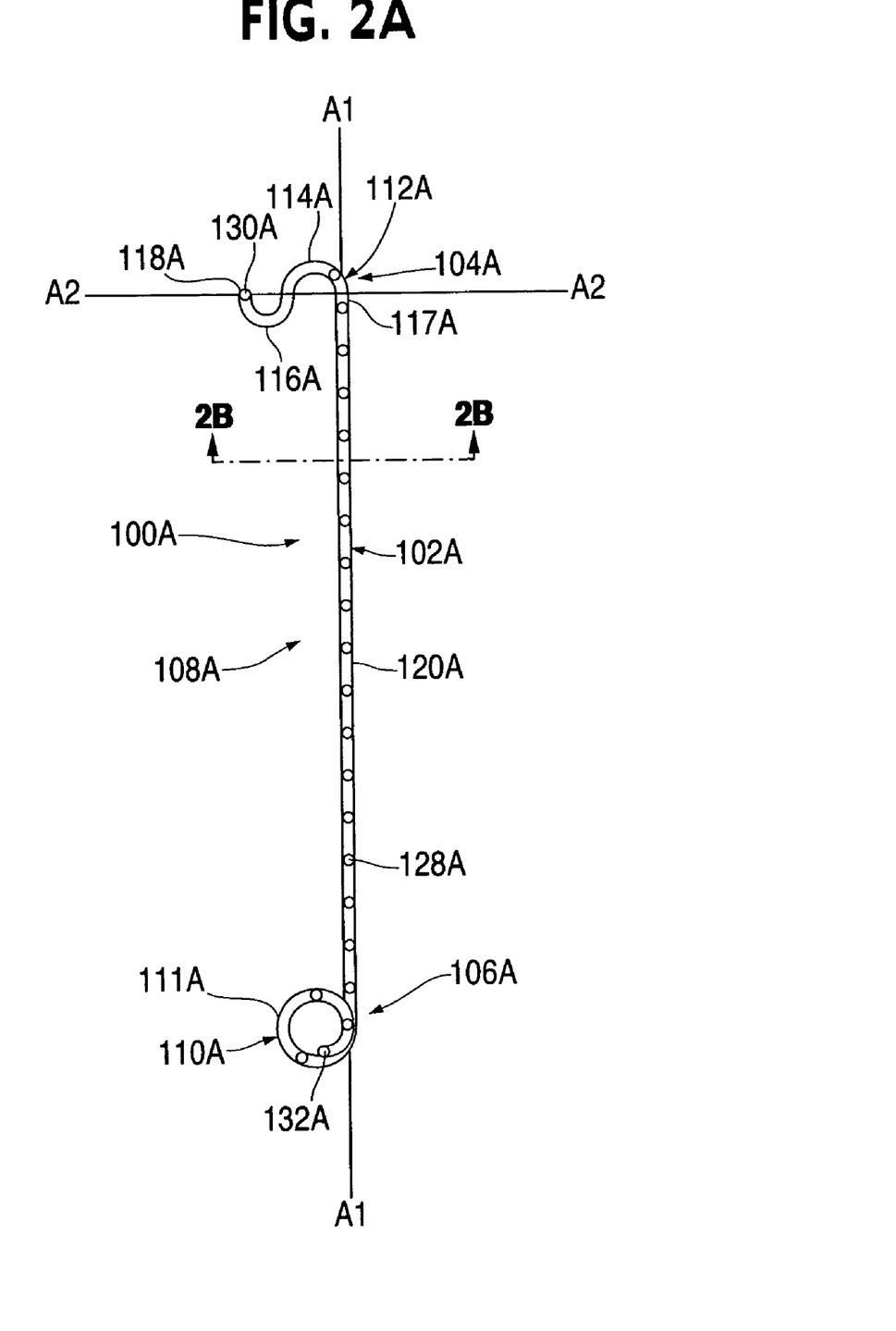
FIG. 2A is perspective view of a ureteral stent according to an embodiment of the invention.

FIG. 2A illustrates an embodiment of the ureteral stent 100A configured to be implanted into a urinary tract of a patient such that the ureteral stent 100A extends from a kidney of the patient to a bladder of the patient. In such an embodiment, the ureteral stent 100A includes an elongate member 102A having a distal end portion 104A, a proximal end portion 106A, and a medial portion 108A. Distal end portion 104A includes a retention portion 112A and is configured to be placed and retained in the kidney of a patient. Proximal end portion 106A includes a retention portion 110A and is configured to be placed and retained in the bladder of the patient.

Retention portion 112A is configured such that it is reconfigurable between a retracted or unconstrained configuration when it is placed in the kidney of a patient, and an extended or constrained configuration when it is being pulled or otherwise forced through the ureter of a patient to remove the stent 100A from the urinary tract of the patient. When the retention portion 112A is in its retracted or unconstrained configuration, the retention portion 112A of the distal end portion 104A is configured to be placed within the kidney of the patient and to help prevent migration of the ureteral stent 100A downwardly toward the bladder. Accordingly the retention portion 112A is configured to help retain at least a portion of the ureteral stent 100A within the kidney of a patient when the retention portion 112A is in its retracted or unconstrained configuration.

FIG. 2A illustrates the retention portion 112A of the distal end portion 104A in its retracted or unconstrained configuration. In the retracted configuration, retention portion 112A has a dimension transverse to an axis A1 defined by elongate member 102A that is sufficient to help retain at least a portion of elongate member 102A in the kidney of the patient. Specifically, the retention portion 112A has an extent along an axis A2 that is disposed at an angle with respect to the axis A1 defined by the elongate member 102A. In the illustrated embodiment, axis A2 intersects axis A1 at substantially a right angle. In other embodiments, axis A2 intersects axis A1 at an angle other than a right angle. In the illustrated embodiment, the retention portion 112A has a sufficiently high moment of inertia and bending modulus to provide an effective degree of resistance to being pulled through the ureter by peristaltic action of the ureter or other bodily processes. In other words, the retention portion 112A is sufficiently large and rigid to substantially maintain its shape when placed within the kidney.

The retention portion 112A includes a first portion 114A, a second portion 116A, a substantially linear portion 117A, and a distal tip 118A that is located at the distal end of the stent 100A. When the distal end retention portion 112A is in a retracted or unconstrained configuration, first portion 114A is curved in a first direction. Similarly, second portion 116A is curved in a second direction. The second direction is substantially opposite the first direction. Accordingly, in the illustrated embodiment, the first portion 114A and the second portion 116A form an approximately sinusoidal shape about axis A2 when the retention portion 112A is in its retracted or unconstrained configuration.

When the retention portion 112A is in its extended or constrained configuration, the retention portion 112A is configured to assume a more linear or elongate, or less tortuous or arcuate, shape. The retention portion 112A is also configured such that when the ureteral stent 100A is removed from the patient by pulling or otherwise forcing the ureteral stent 100A through the urinary tract, the retention portion 112A is passed through the ureter U such that the distal tip 118A is disposed away from a sidewall SW of the ureter U (see FIG. 3).

Figure 3:
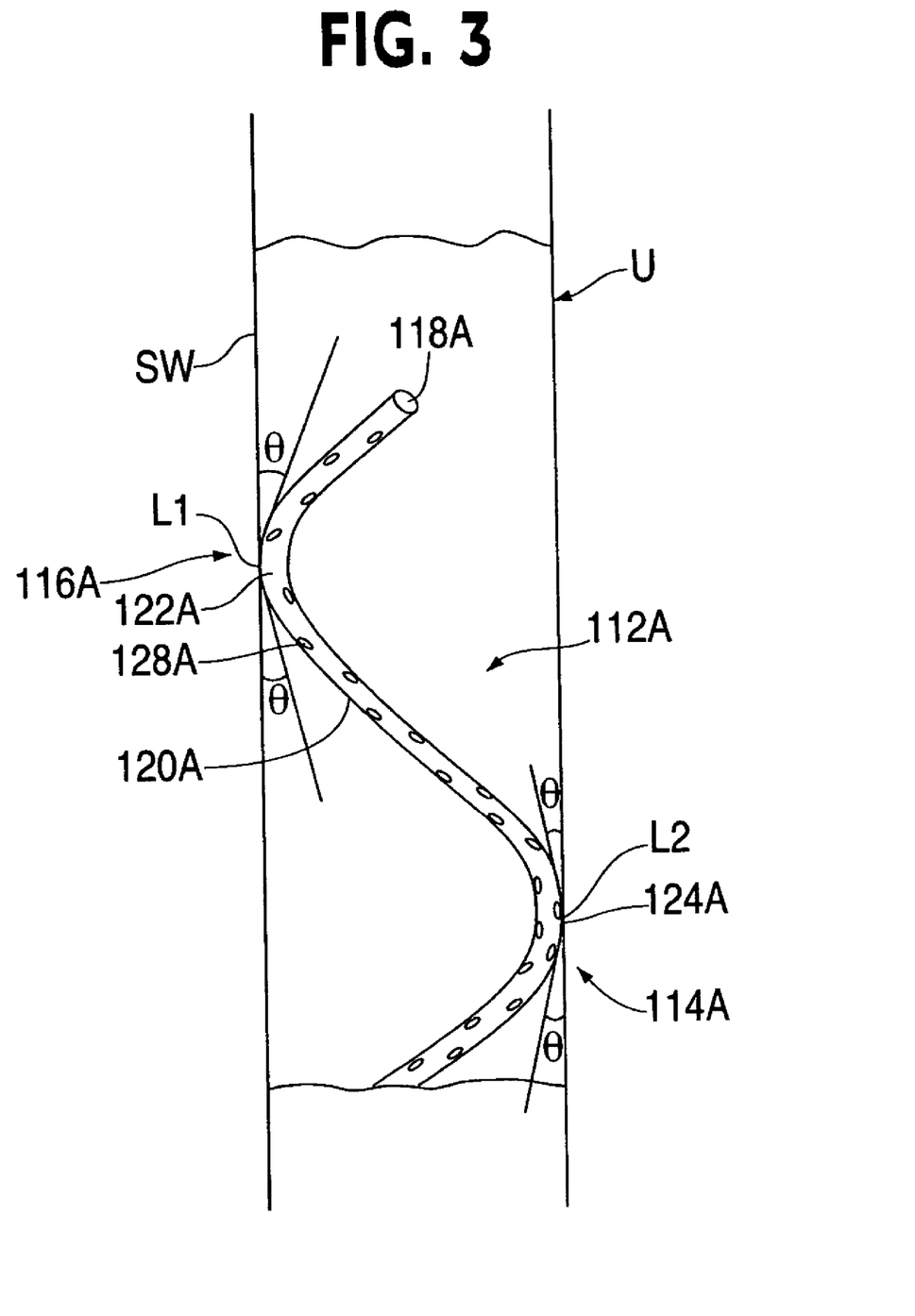
FIG. 3 is a side view of the distal end portion of the ureteral stent of FIG. 2A shown positioned within a ureter.

FIG. 3 illustrates retention portion 112A in its extended or constrained configuration. The retention portion 112A assumes its extended or constrained configuration when the elongate member 102A is being removed from the kidney and passed through the ureter U of the patient. In the extended configuration, the first portion 114A and the second portion 116A reconfigure to a location within the ureter U of the patient such that distal tip 118A is positioned a distance from the sidewall SW of the ureter U. In other words, the distal tip 118A is spaced from the sidewall SW of the ureter U when the ureteral stent 100A is removed from the urinary tract of the patient. Additionally, when the ureteral stent 100A is removed from the urinary tract of the patient, no portion of retention portion 112A engages the sidewall SW of the ureter U at an angle θ greater than 90 degrees, the angle θ being measured between retention portion 112A and the sidewall SW of the ureter U on the distal side of a point of contact between the ureteral stent 100A and the sidewall SW of the ureter U (see FIG. 3).

In this extended configuration, distal tip 118A will be allowed to move freely through the ureter U as elongate member 102A is pulled through the ureter U and removed from the patient. Thus, ureteral stent 100A will contact the sidewall SW of the ureter U at a first contact portion 122A and a second contact portion 124A. As shown in FIG. 3, first contact portion 122A is disposed between distal tip 118A and second contact portion 124A, and contacts the ureter U at a location L1 of sidewall SW. The second contact portion 124A contacts ureter U at a location L2 of sidewall SW. Because the distal tip 118A is disposed away from the sidewall SW of the ureter U, the distal tip 118A will move freely within the ureter U. In other words, the distal tip 118A does not drag along the sidewall SW of the ureter U when the ureteral stent 100A is removed from the patient.

The retention portion 110A of the proximal end portion 106A of the ureteral stent 100A is configured to be placed within the bladder of the patient and to help prevent migration of the ureteral stent 100A upwardly toward the kidney of the patient. Accordingly, the retention portion 110A is configured to help retain at least a portion of the ureteral stent 100A within the bladder of the patient. In the illustrated embodiment, as shown in FIG. 2A, retention portion 110A includes a pigtail portion 111A. In other embodiments, the retention portion of the proximal end portion includes a loop portion, a "J" hook portion, a curled portion, a spiral portion, or any other structure that is configured to retain at least a portion of the ureteral stent within the bladder of the patient.

Figure 2B:
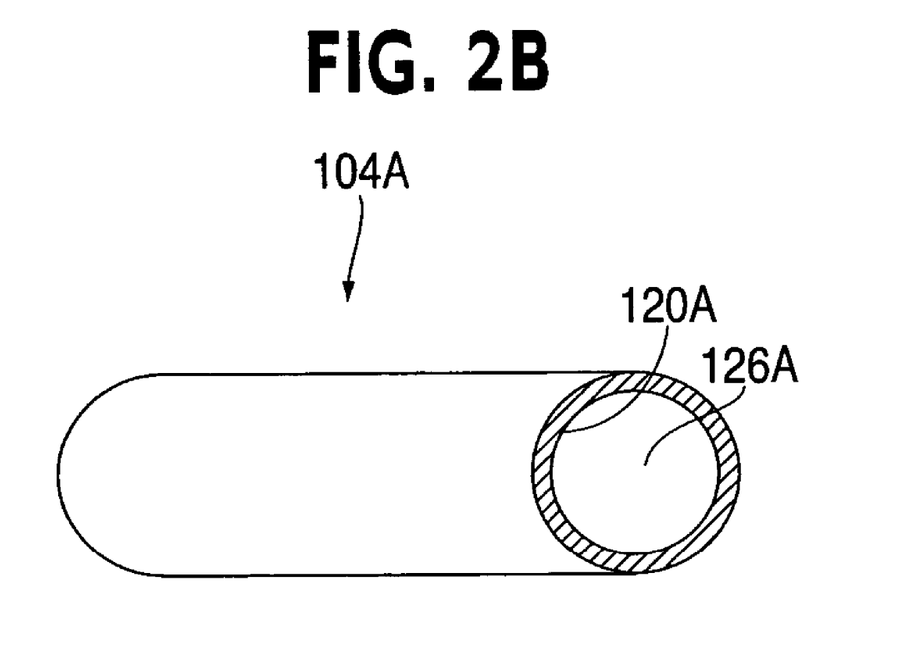
FIG. 2B is a cross sectional view taken along line 2B-2B in FIG. 2A.

As shown in FIGS. 2A and 2B, ureteral stent 100A includes a sidewall 120A that defines a lumen 126A. The lumen 126A extends from the distal end portion 104A to the proximal end portion 106A of the ureteral stent 100A and is configured to convey a liquid, such as urine, from the distal end portion 104A to the proximal end portion 106A. In the illustrated embodiment, the ureteral stent 100A defines an opening 130A at the distal end portion 104A and an opening 132A at the proximal end portion 106A. The openings 130A and 132A communicate with the lumen 126A. The ureteral stent 100A also includes side ports or side openings 128A defined by the sidewall 120A. The side ports or side openings 128A defined by sidewall 120A provide fluid communication between the exterior of the ureteral stent 100A and the lumen 126A. Side ports or side openings 128A may be located anywhere on ureteral stent 100A, including but not limited to, along elongate member 102A, on distal end portion 104A, on proximal end portion 106A.

In one embodiment, the thickness of the sidewall 120A may be between about 0.25 mm (0.01 inches) and 0.50 mm (0.02 inches), the diameter of the lumen between about 1.0 mm (0.04 inches) and 1.3 mm (0.05 inches), and the outside diameter between about 1.8 mm (0.07 inches) and 2.3 mm (0.09 inches) or between about 5 and 7 French. In another embodiment, the thickness of the sidewall may be larger than 0.50 mm. In another embodiment, the thickness of the sidewall may be less than 0.25 mm. In yet another embodiment, the thickness of the sidewall varies from one end portion of the ureteral stent to another end portion of the ureteral stent.

The ureteral stent 100A may be formed from a number of different biocompatible materials. The ureteral stent 100A may consist of one material or may be formed, for example by extrusion, of two or more materials along its length. For example, in one embodiment, the distal end portion 104A of the ureteral stent 100A is formed from a first material having a first durometer and the proximal end portion 106A is formed from a second material, which is softer and/or more flexible than the first material, having a second durometer different than the first durometer. Accordingly, the proximal end portion 106A may be made of a softer or more flexible material than that of the distal end 104A and vice versa.

The ureteral stent 100A may be formed from any material or materials known in the art to be used in constructing ureteral stents. One subset of biocompatible materials best suited for the ureteral stent 100A exhibit at least some of the following characteristics: high tensile strength, high retention coil strength, excellent biocompatibility and biodurability, excellent radiopacity or fluoroscopic visibility, availability in varying durometers, and a low resistance to passage. For example, in one embodiment, the ureteral stent 100A is formed from a polymeric material.

Figure 4:
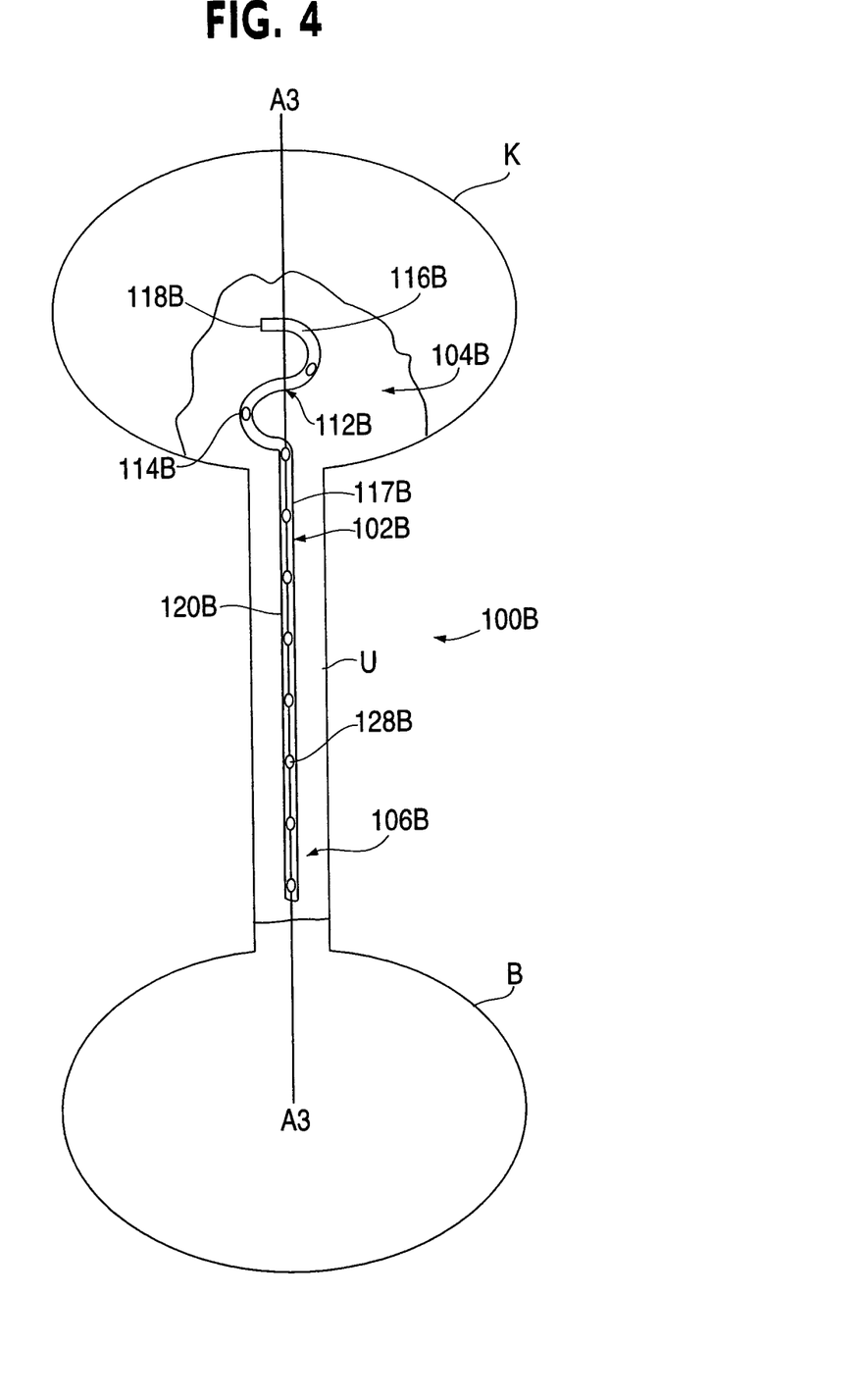
FIG. 4 is a perspective view of a ureteral stent according to an embodiment of the invention shown within a urinary tract.

FIG. 4 illustrates a ureteral stent 100B according to another embodiment of the invention. The ureteral stent 100B includes an elongate member 102B having a distal end portion 104B, a proximal end portion 106B and a medial portion 108B. The ureteral stent 100B illustrated in FIG. 4 is configured to extend from a kidney K of the patient to a ureter U of the patient. The distal end portion 104B is configured to be placed and retained in the kidney K of the patient and the proximal end portion 106B is configured to be placed within the ureter U of the patient. As with the previous embodiments, the ureteral stent 100B is a tubular member and includes a sidewall 120B that defines a lumen (not illustrated). The lumen extends from one end of the elongate member 102B to another end of the elongate member 102B. Ureteral stent 100B also includes ports or openings 128B defined by the sidewall 120B.

A retention portion 112B is disposed at the distal end portion 104B of the stent 100B. The retention portion 112B has a retracted or unconstrained configuration and an extended or constrained configuration. The retention portion 112B includes a first portion 114B, a second portion 116B, and a substantially linear portion 117B. When the distal end retention portion 112B is in a retracted or unconstrained configuration, first portion 114B is curved in a first direction. Similarly, second portion 116B is curved in a second direction. The second direction is substantially opposite the first direction. Accordingly, the first portion 114B and the second portion 116B form an approximately sinusoidal shape about an axis A3, which is defined by the elongate member 102B of the ureteral stent 1001B.

When the retention portion 112B is in its extended or constrained configuration, the retention portion 112B is configured to assume a more linear or elongate shape. Accordingly, the retention portion 112B is configured such that when the ureteral stent 100B is removed from the patient by pulling or otherwise forcing the ureteral stent 100B through the urinary tract, the retention portion 112B is passed through the ureter U such that a distal tip 118B of the ureteral stent 100B is disposed away from the sidewall of the ureter U.

Figure 5A:
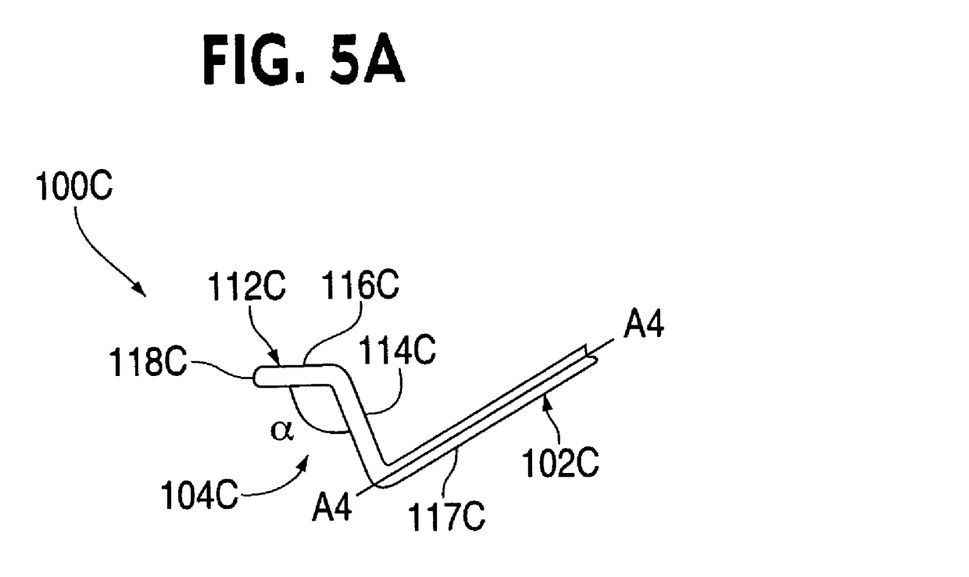
FIG. 5A is a side view of a distal end portion of a ureteral stent according to an embodiment of the invention.
Figure 5B:
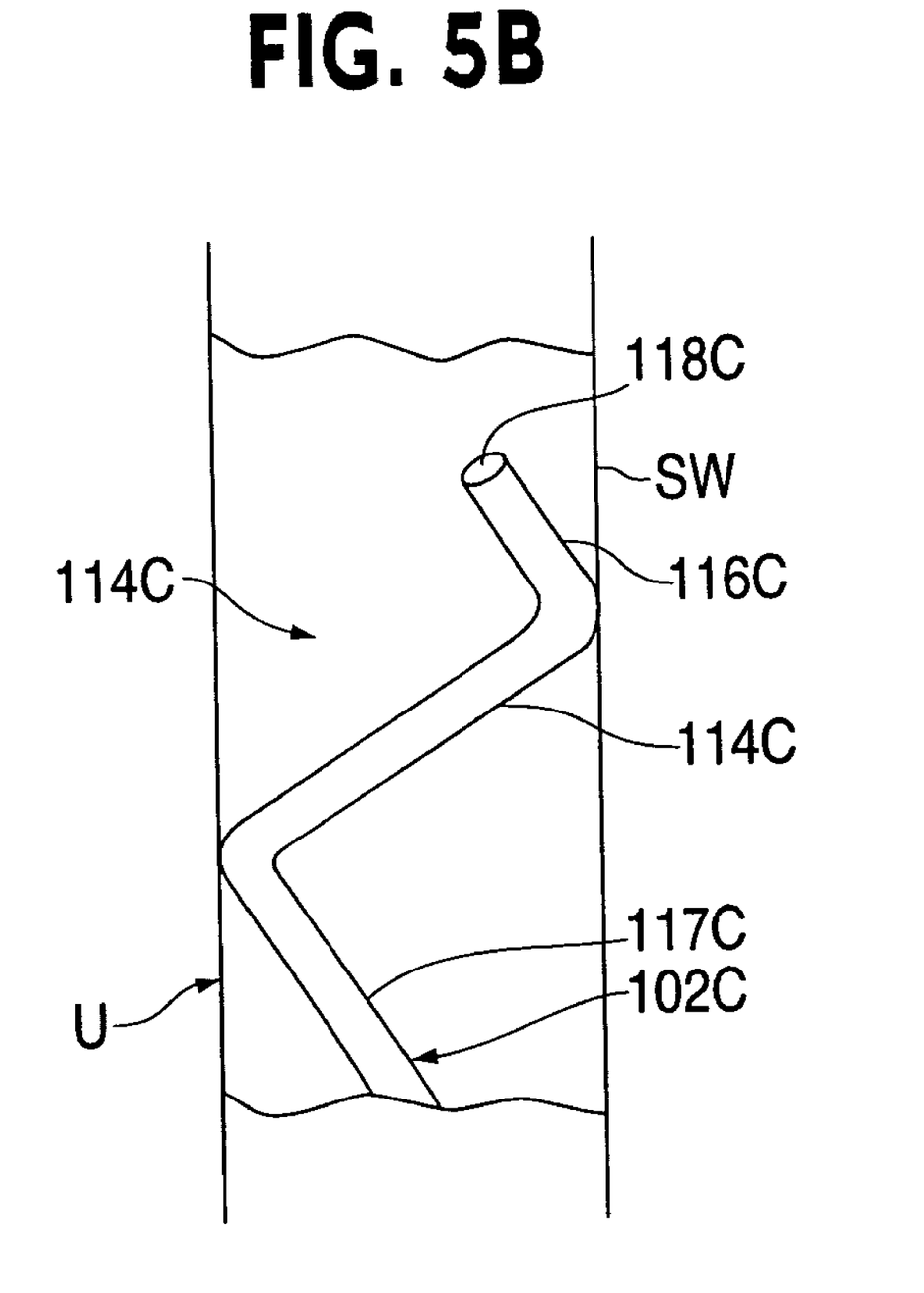
FIG. 5B is a side view of the distal end portion of the ureteral stent of FIG. 5A shown within a ureter.

FIGS. 5A and 5B illustrate a distal portion 104C of a ureteral stent 100C according to another embodiment of the invention. The ureteral stent 100C includes an elongate member 102C and a retention portion 112C disposed at the distal portion 104C of the stent 100C. The retention portion 112C has a retracted or unconstrained configuration, as shown in FIG. 5A, and an extended or constrained configuration, as shown in FIG. 5B. When the retention portion 112C is in its retracted configuration, the retention portion 112C has a dimension transverse to an axis A4 defined by the elongate member 102C that is sufficient to help retain at least a portion of the ureteral stent 100C within the kidney of the patient. When the retention portion 112C is in its extended or constrained configuration, the retention portion 112C assumes a more linear or elongate shape.

The retention portion 112C includes a first portion 114C, a second portion 116C and a third portion 117C. When retention portion 112C is in its retracted configuration, first portion 114C is substantially linear and extends substantially perpendicularly from the third portion 117C. Similarly, second portion 116C is substantially linear and extends from first portion 114C. In the illustrated embodiment, the second portion 116C and the first portion 114C form an angle α that is obtuse. In another embodiment, the second portion and first portion form an angle other than an obtuse angle.

As best illustrated in FIG. 5B, as ureteral stent 100C is removed from the kidney of the patient, the retention portion 112C reconfigures within the ureter U of the patient to its extended or constrained configuration. In such a configuration, a distal tip 118C of the ureteral stent 100C is positioned at a spaced distance from a sidewall SW of the ureter U of the patient.

Figure 6A:
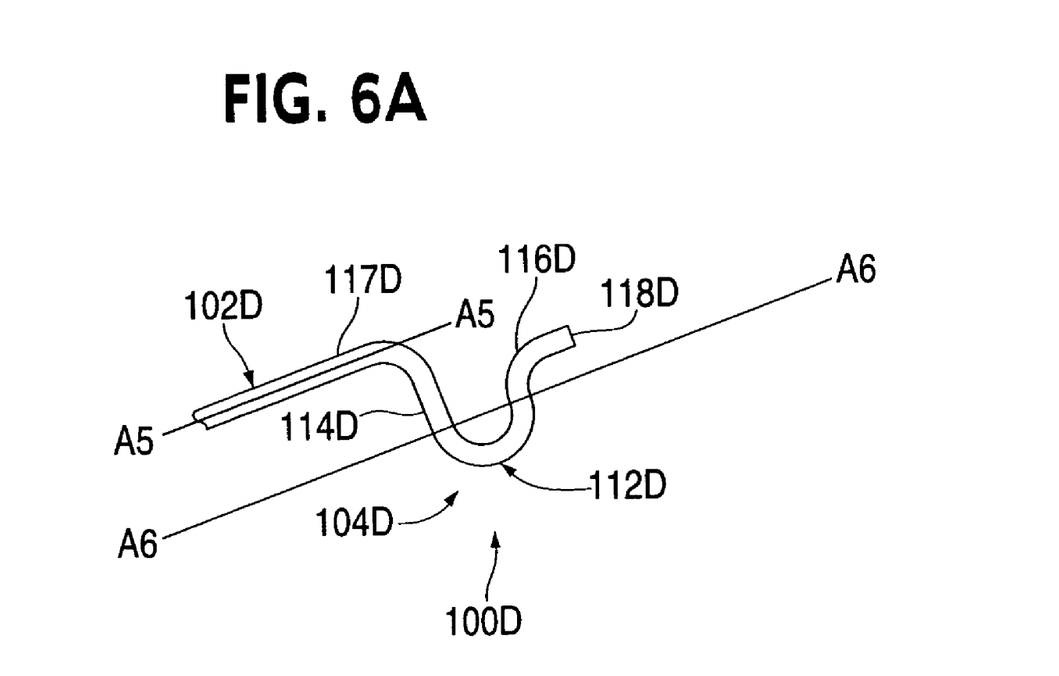
FIG. 6A is a side view of a distal end portion of an embodiment of a ureteral stent according to an embodiment of the invention.
Figure 6B:
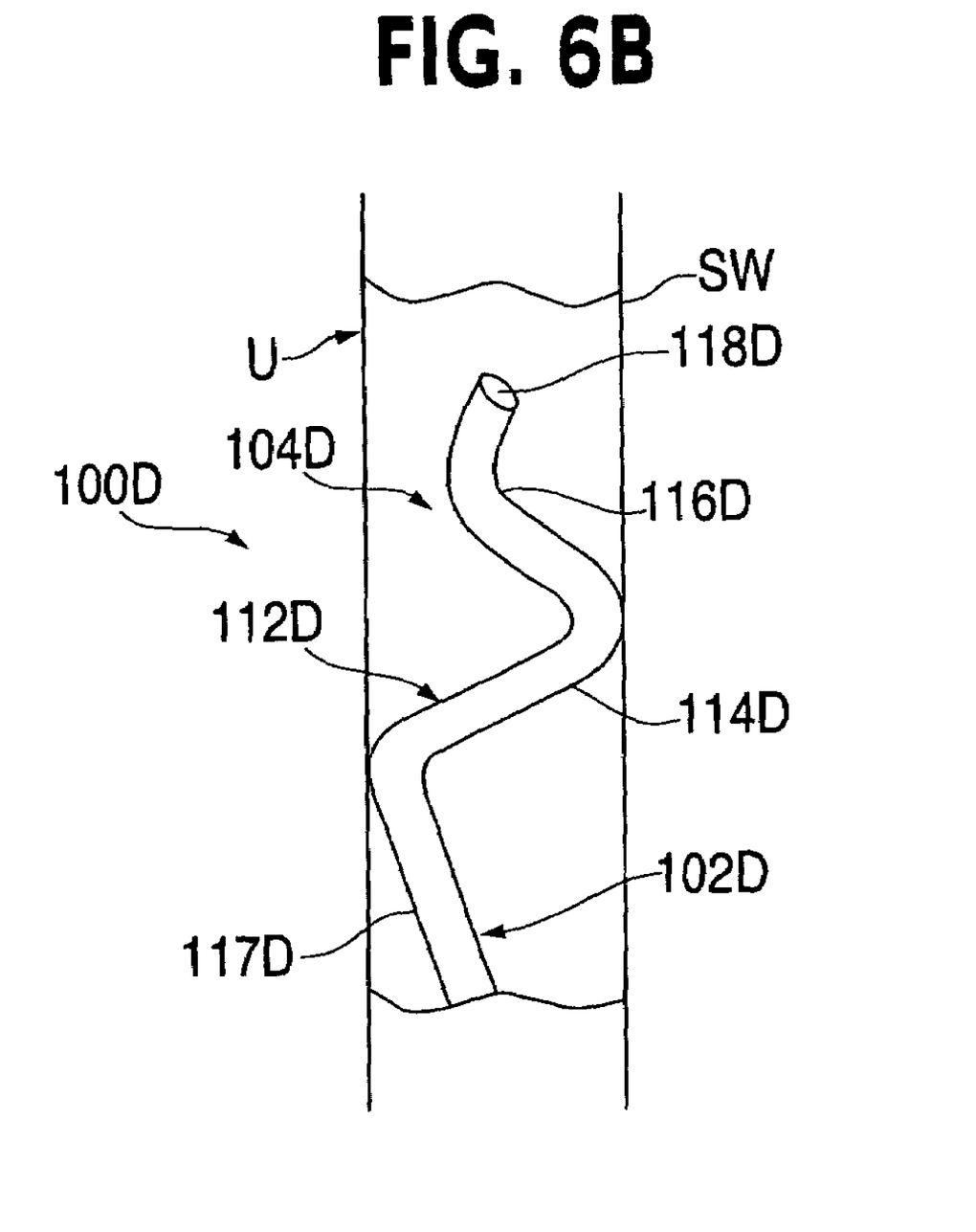
FIG. 6B is a side view of the distal end portion of the ureteral stent of FIG. 6A shown within a ureter.

FIGS. 6A and 6B illustrate a distal portion 104D of a ureteral stent 100D according to another embodiment of the invention. The ureteral stent 100D includes an elongate member 102D and a retention portion 112D disposed at the distal portion 104D of the stent 100D. The retention portion 112D has a retracted or unconstrained configuration and an extended or constrained configuration. When the retention portion 112D is in its retracted configuration, the retention portion 112D has a dimension transverse to an axis A5 defined by the elongate member 102D that is sufficient to help retain at least a portion of the ureteral stent 100D within the kidney of the patient. When the retention portion 112D is in its extended or constrained configuration, retention portion 112D is configured to assume a more linear or elongate shape.

The retention portion 112D includes a first portion 114D, a second portion 116D and a third portion 117D. When retention portion 112D is in its retracted configuration, first portion 114D is substantially linear and extends substantially perpendicularly from the elongate member 102D, as shown in FIG. 6A. Second portion 116D extends from the first portion 114D and includes a substantially sinusoidal shape. Specifically, the retention portion 112D includes a tortuous or arcuate shape that is substantially sinusoidal and that undulates about an axis A6 that is substantially parallel to the axis A5 defined by the elongate member 102D.

As best illustrated in FIG. 6B, as ureteral stent 100D is removed from the kidney of the patient, the retention portion 112D reconfigures within the ureter of the patient to its extended or constrained configuration. In such a configuration, a distal tip 118D of the ureteral stent 100D is positioned at a spaced distance from a sidewall SW of the ureter U of the patient.

Figure 7A:
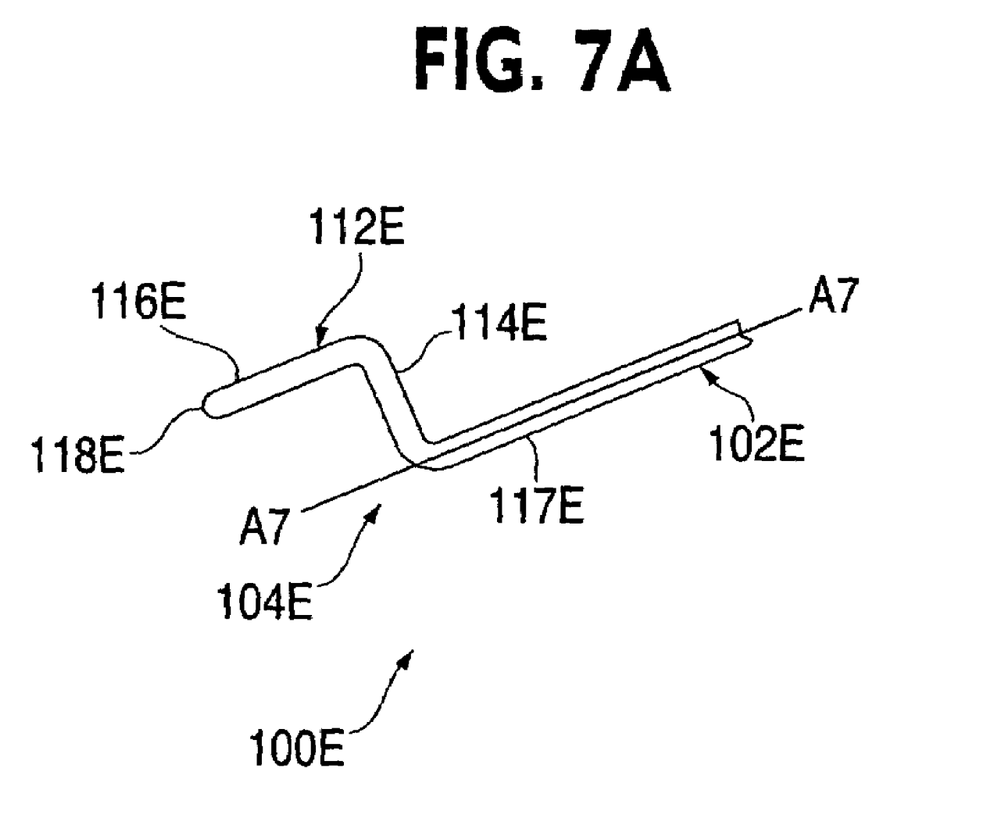
FIG. 7A is a side view of a distal end portion of an embodiment of a ureteral stent according to an embodiment of the invention.
Figure 7B:
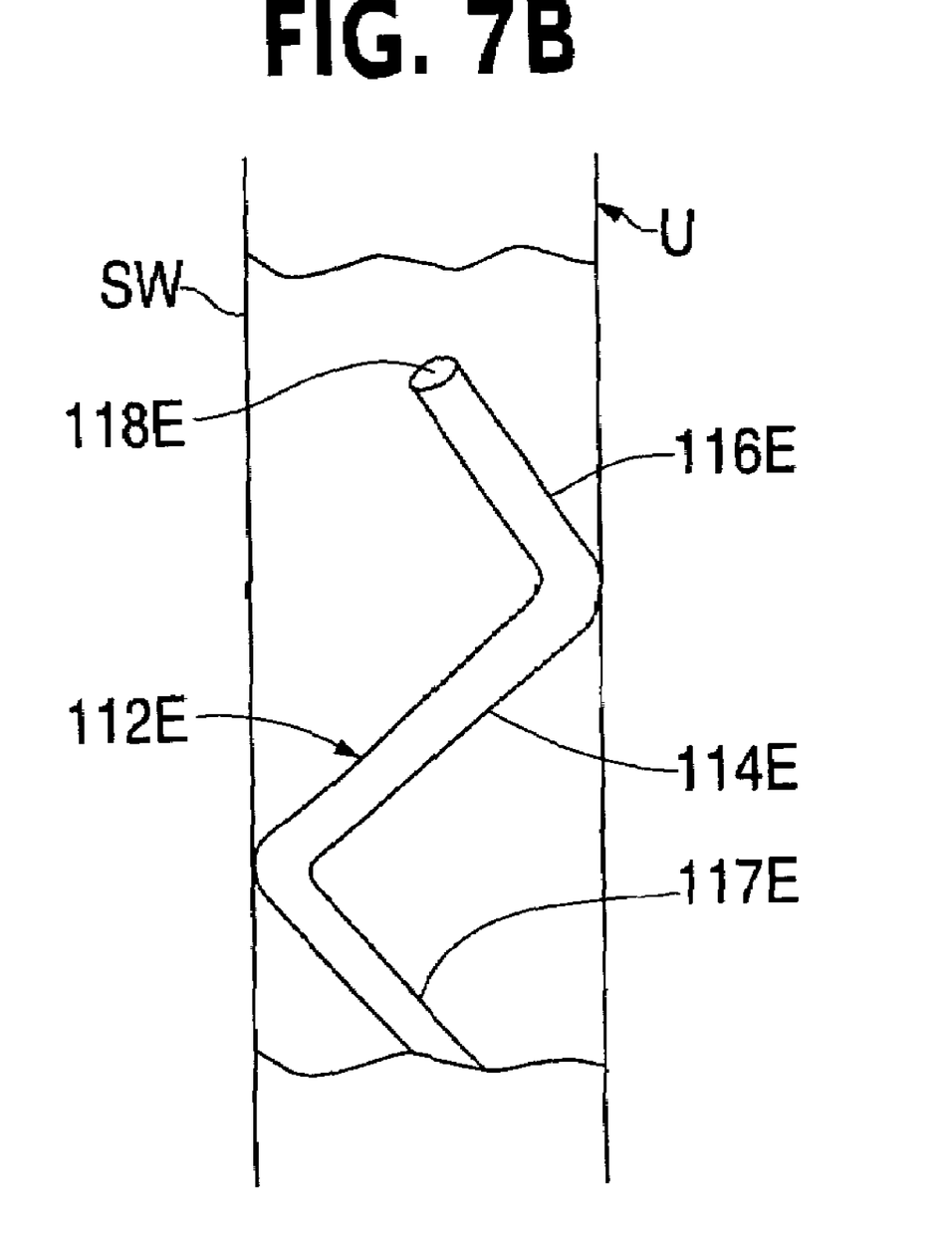
FIG. 7B is a side view of the distal end portion of the ureteral stent of FIG. 7A shown within a ureter.

FIGS. 7A and 7B illustrate a distal portion 104E of a ureteral stent 100E according to another embodiment of the invention. The ureteral stent 100E includes an elongate member 102E and a retention portion 112E disposed at the distal portion 104E of the stent 100E. The retention portion 112E has a retracted or unconstrained configuration, as shown in FIG. 7A, and an extended or constrained configuration, as shown in FIG. 7B. When the retention portion 112E is in its retracted configuration, the retention portion 112E has a dimension transverse to an axis A7 defined by the elongate member 102E that is sufficient to help retain at least a portion of the ureteral stent 100E within the kidney of the patient. When the retention portion 112E is in its extended or constrained configuration, retention portion 112E is configured to assume a more linear or elongate shape.

The retention portion 112E includes a first portion 114E, a second portion 116E, and a third portion 117E. When retention portion 112E is in its retracted configuration, first portion 114E is substantially linear and extends substantially perpendicularly from the third portion 117E. Second portion 116E is substantially linear and extends substantially perpendicularly from the first portion 114E. Accordingly, the second portion 116E extends in a direction substantially parallel to both the axis A7 defined by the elongate member 102E of the ureteral stent 100E and to the third portion 117E.

As best illustrated in FIG. 7B, as ureteral stent 100E is removed from the kidney of the patient, the retention portion 112E reconfigures within the ureter of the patient to its extended or constrained configuration. In such a configuration, a distal tip 118E of the distal end retention portion 112E, is positioned at a spaced distance from a sidewall of the ureter of the patient.

The principles, embodiments, and modes of operation of the present invention have been described in the foregoing description. However, the invention that is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims be embraced thereby.

What is claimed is:

1. A ureteral stent, comprising:
an elongate member having a distal end portion for placement within a kidney of a patient and a proximal end portion for placement in at least one of a ureter of the patient and a bladder of the patient, the distal end portion having a retention portion configured to help retain at least a portion of the elongate member in the kidney of the patient, the retention portion defines an axis transverse to an axis defined by the elongate member, the retention member including a first curved portion curving in a first direction away from the axis of the retention member and a second portion curving in a second direction opposite the first direction,
the elongate member being configured to be passed through the ureter of the patient from the kidney to the bladder to remove the elongate member from the patient, the distal end portion being configured such that a distal tip of the distal end portion is spaced from a sidewall of the ureter when the elongate member is passed through the ureter of the patient to remove the elongate member from the patient.

2. The ureteral stent of claim 1, wherein the elongate member includes a first contact portion and a second contact portion, the first contact portion and the second contact portion are configured to contact the sidewall of the ureter when the elongate member is passed through the ureter of the patient to remove the elongate member from the patient, the first contact portion being disposed between the second contact portion and the distal tip.

3. The ureteral stent of claim 1, wherein the retention portion has a dimension transverse to the axis defined by the elongate member sufficient to help retain at least a portion of the elongate member in the kidney of the patient.

4. The ureteral stent of claim 1, wherein the proximal end portion includes a retention portion configured to help retain at least a portion of the elongate member in the bladder of the patient.

5. A ureteral stent, comprising:
an elongate member configured to be placed within a patient and extend from a kidney of the patient to at least one of a ureter of a patient and a bladder of a patient, the elongate member including a medial portion and a retention portion, the retention portion reconfigurable between a retracted configuration and an extended configuration, the retention portion defining an axis transverse to an axis defined by the medial portion of the elongate member and including a first portion curved in a first direction away from the axis of the retention portion and a second portion curved in a second direction opposite the first direction when the retention portion is in its retracted configuration, the retention portion having a dimension transverse to the axis defined by the medial portion of the elongate member when the retention portion is in its retracted configuration sufficient to help retain at least a portion of the elongate member in the kidney of the patient, the elongate member being configured to be passed through the ureter of the patient from the kidney to the bladder to remove the elongate member from the patient, the retention portion being configured such that a distal tip of the retention portion is spaced from a sidewall of the ureter when the elongate member is passed through the ureter of the patient to remove the elongate member from the patient.

6. The ureteral stent of claim 5, wherein the elongate member is configured to contact the sidewall of the ureter at a first location and at a second location when the elongate member is passed through the ureter of the patient to remove the elongate member from the patient, the first location being disposed between the second location and the kidney of the patient.

7. The ureteral stent of claim 5, wherein the elongate member includes a first contact portion and a second contact portion, the first contact portion and the second contact portion are configured to contact the sidewall of the ureter when the elongate member is passed through the ureter of the patient to remove the elongate member from the patient, the first contact portion being disposed between the second contact portion and the distal tip.

8. The ureteral stent of claim 5, the retention portion being a first retention portion, wherein the first retention portion is located adjacent a distal end portion of the elongate member, the elongate member including a second retention portion located adjacent a proximal end portion of the elongate member, the second retention portion being configured to help retain at least a portion of the elongate member in the bladder of the patient.

9. A ureteral stent comprising:
an elongate member having a proximal end portion for placement in at least one of a ureter of a patient and a bladder of the patient, a distal end portion for placement in a kidney of the patient, and a medial portion located between the proximal end portion and the distal end portion, the medial portion defining an axis,
the distal end portion having a retention portion configured to help retain at least a portion of the elongate member in the kidney of the patient, the retention portion having a curved portion, the curved portion being substantially sinusoidal in shape and defining an axis transverse to an axis of the medial portion of the elongate member, the curved portion of the retention portion including a first curved portion and a second curved portion each curving in a direction away from the axis defined by the curved portion.

10. The ureteral stent of claim 9, wherein the proximal end portion is configured to be placed in the bladder of the patient, the proximal end portion having a retention portion configured to help retain at least a portion of the elongate member in the bladder of the patient.

11. The ureteral stent of claim 9, wherein the elongate member includes a sidewall that defines a lumen.

12. The ureteral stent of claim 9, wherein the elongate member includes a sidewall that defines a lumen, the lumen extends from the proximal end portion of the elongate member to the distal end portion of the elongate member.

13. The ureteral stent of claim 9, wherein the elongate member includes a sidewall that defines a lumen, the lumen is configured to convey liquid.

14. The ureteral stent of claim 9, wherein the elongate member includes a sidewall that defines a lumen, the sidewall having at least one opening that communicates with the lumen.

15. The ureteral stent of claim 9, wherein the elongate member includes a lumen, the proximal end portion includes an opening that communicates with the lumen, the distal end portion includes an opening that communicates with the lumen.

16. The ureteral stent of claim 9, wherein an amplitude of the substantially sinusoidal shape is greater than a width of a ureter.

17. A ureteral stent, comprising:
an elongate body portion defining an axis, the elongate body portion having a dimension transverse to the axis defined by the elongate body portion being less than a width of a lumen of a human ureter; and
a distal end retention member coupled to a distal end portion of the elongate body portion having an unconstrained configuration in which the shape is tortuous and has a dimension transverse to the axis defined by the elongate body portion sufficiently greater than the width of a human ureter, the distal end retention member has a sufficiently high bending modulus to provide an effective degree of resistance to being pulled through the ureter by peristaltic action of the ureter or other bodily process, and when disposed completely within the ureter, a distal tip of the distal end retention member is spaced from a wall of the ureter and the distal end retention member assumes a constrained configuration in which no portion of the distal end retention member engages the wall of the ureter at an angle greater than 90 degrees, the angle being measured between the distal end retention member and the wall of the ureter on the distal side of a contact point.

18. The ureteral stent of claim 17, further comprising:
a proximal end retention member coupled to a proximal end portion of the elongate body portion and configured to help retain at least a portion of the ureteral stent in the bladder of the patient.

19. The ureteral stent of claim 17, wherein the tortuous shape of the distal end retention member extends along an axis transverse to the axis of the elongate body portion.

20. The ureteral stent of claim 17, wherein the distal end retention member defines an axis transverse to the axis of the elongate body portion and includes a first portion curving in a first direction away from the axis of the distal end retention member and a second portion curving in a second direction opposite the first direction.

* * * * *